United States Patent [19]
Urick et al.

[11] Patent Number: 5,497,783
[45] Date of Patent: Mar. 12, 1996

[54] GUIDEWIRE HAVING RADIOSCOPIC TIP

[75] Inventors: Michael J. Urick; Richard R. Prather, both of Rogers; John H. Randby, Eagan, all of Minn.

[73] Assignee: SciMed Life Systems, Inc., Maple Grove, Minn.

[21] Appl. No.: 245,726

[22] Filed: May 18, 1994

[51] Int. Cl.⁶ .................................................. A61B 5/00
[52] U.S. Cl. ........................................... 128/772; 128/657
[58] Field of Search ................................. 128/657, 772; 604/164, 170, 280, 282

[56] References Cited

U.S. PATENT DOCUMENTS

| | | | |
|---|---|---|---|
| 3,749,086 | 7/1973 | Kline et al. | 128/772 |
| 3,906,938 | 9/1975 | Fleischhacker | 128/772 |
| 4,456,017 | 6/1984 | Miles | 128/772 |
| 4,538,622 | 9/1985 | Samson et al. | 128/772 |
| 4,545,390 | 10/1985 | Leary | 128/772 |
| 4,554,929 | 11/1985 | Samson et al. | 128/772 |
| 4,619,274 | 10/1986 | Morrison | 128/749 |
| 4,719,924 | 1/1988 | Crittenden et al. | 128/772 |
| 4,721,117 | 1/1988 | Mar et al. | 128/772 |
| 4,724,846 | 2/1988 | Evans, III | 128/772 |
| 4,748,986 | 6/1988 | Morrison et al. | 128/772 |
| 4,763,647 | 8/1988 | Gamble | 128/772 X |
| 4,811,743 | 3/1989 | Stevens | 128/772 |
| 4,813,434 | 3/1989 | Buchbinder et al. | 128/772 |
| 4,830,023 | 5/1989 | de Toledo et al. | 128/772 |
| 4,846,186 | 7/1989 | Box et al. | 128/657 |
| 4,846,193 | 7/1989 | Tremulis et al. | 128/772 |
| 4,867,173 | 9/1989 | Leoni | 128/772 |
| 4,922,924 | 5/1990 | Gambale et al. | 128/772 |
| 4,934,380 | 6/1990 | de Toledo | 128/772 |
| 4,971,490 | 11/1990 | Hawkins | 128/772 |
| 5,001,825 | 3/1991 | Halpern | 29/456 |
| 5,002,559 | 3/1991 | Tower | 606/194 |
| 5,037,391 | 8/1991 | Hammerslag et al. | 604/95 |
| 5,054,501 | 10/1991 | Chuttani et al. | 128/772 |
| 5,060,660 | 10/1991 | Gambale et al. | 128/772 |
| 5,063,935 | 11/1991 | Gambale | 128/657 |
| 5,065,769 | 11/1991 | de Toledo | 128/772 |
| 5,067,489 | 11/1991 | Lind | 128/772 |
| 5,135,503 | 8/1992 | Abrams | 128/772 X |
| 5,144,959 | 9/1992 | Gambale et al. | 128/772 |
| 5,147,317 | 9/1992 | Shank et al. | 604/164 |
| 5,174,302 | 12/1992 | Palmer | 128/772 |
| 5,211,636 | 5/1993 | Mische | 604/264 |
| 5,228,453 | 7/1993 | Sepetka | 128/772 |
| 5,243,996 | 9/1993 | Hall | 128/772 |
| 5,259,393 | 11/1993 | Corso, Jr. et al. | 128/772 |

FOREIGN PATENT DOCUMENTS

92/09072  3/1992  WIPO .................... 128/772

*Primary Examiner*—Sam Rimell
*Attorney, Agent, or Firm*—Nawrocki, Rooney & Sivertson

[57] ABSTRACT

An apparatus for and method of making a guide wire for use in medical procedures in general and cardiovascular procedures in particular. A core wire is formed as the inner member. A distal helix is fixedly attached to the distal end of the core wire. The core wire has tapers or is continuously tapered to achieve the desired handling characteristics. The distal helix is space wound, space wound and close wound, double wound, and/or ground to provide the desired radioscopic signature.

11 Claims, 8 Drawing Sheets

GUIDEWIRE HAVING RADIOSCOPIC TIP

BACKGROUND OF THE INVENTION

1. Field of the Invention

The present invention relates in general to medical instrumentation, and more particularly to intraluminal devices, and still more particularly to guidewires or core wires for intraluminal devices including catheters.

2. Description of the Prior Art

The use of intraluminal catheters for treatment of various medical problems within the body is well known. It is also well known that a variety of problems are encountered as the catheter is steered through the selected lumen to a desired point within the body. The path may be tortuous and the point of interest may be difficult to locate precisely. To combat this problem, a flexible guidewire may first be inserted into the vascular lumen to the desired location. Once a guidewire is in positioned, a desired catheter may then be slid over the guidewire to reach the desired situs in the body.

It can readily be seen that it is important to have a guidewire that is flexible enough to traverse the tortuous vascular system. It can also be readily be seen that it is also important to have a guidewire that is radioscopic such that the physician can verify the position of the guidewire within the vascular lumen.

A continuing series of technical improvements and additions have been made in the catheter field to provide devices and methods which can overcome certain of the difficulties. One such series of improvements has resulted in the now well known use of a thin flexible guidewire that can be more easily steered through the lumen by forces applied to a proximal section. Because the distal section of a tapered guidewire may lose pushability, another improvement that has been developed is the use of a coiled wire helix which is wrapped around the most distal section of the guidewire. The coiled wire helix may improve the pushability of the distal section of the guidewire while maintaining overall flexibility.

One improvement involving a coiled wire helix is discussed in U.S. Pat. No. 4,619,274 issued to Morrison. Morrison discloses a core member having a proximal and a distal end wherein the core member has a decreasing cross sectional area in a direction towards the distal end. The decreasing cross sectional area is incremental in that the core member comprises a plurality of fixed diameter cylinders which are coupled together by "tapered sections". The diameters of the fixed diameter cylinders become smaller in the direction of the distal end of the core member.

Morrison further discloses a tapered coil which is carried and secured to the core element and extends over the distal extremity of the core element. The tapered coil has a proximal end and a distal end wherein the diameter of the tapered coil decreases in the direction towards the distal end. Furthermore, the coil is formed of wire having a diameter which decreases in the direction towards the distal end. The improvements suggested by Morrison may provide some increased pushability while maintaining a degree of flexibility. However, the decreasing diameter core member and tapered coil may limit the controllability of the distal tip of the core member. Also, the apparatus suggested in Morrison may only provide a single radioscopic intensity level within the vascular lumen.

Another technique involving a coiled wire helix is discussed in U.S. Pat. No. 4,846,186 issued to Box et al. In Box, a core member having an initial uniform diameter segment tapers along a uniform portion to a second constant diameter segment. A flexible spring tip surrounds and is attached to the second constant diameter segment and extends distally therefrom. The core member again tapers in a region where the flexible spring separates from the core member. Within the flexible spring, the core member is flattened to increase the flexibility of the distal portion of the core member. The flattened core and spring are brazed together at an extreme distal tip portion to form a distal guidewire tip. A problem with Box is that the flexibility of the core member is not uniformly increased in the direction of the distal tip. That is, the Box apparatus comprises a plurality of uniform diameter segments coupled together with tapered portions. Therefore, the change in flexibility is isolated to discrete locations along the core member. Another problem with Box is that the radioscopic image has a single radioscopic intensity level within the vascular lumen.

A further approach involving a coiled wire helix is discussed in U.S. Pat. No. 4,971,490 issued to Hawkins. Hawkins suggests a method for providing a smooth transition from the proximal end of the coiled wire helix to the core member. In previous embodiments, the coiled wire helix was wound around the core member thereby creating a ridge at the interface between the coil and the core member. This ridge may cause friction against the vascular lumen as the core member is withdrawn from the vascular lumen. Hawkins provides for a stepped down portion near the distal end of the core member defining a reduced diameter for receiving the proximal end of the coiled wire helix. The reduced diameter is set to be less than the inner diameter of the coil wire helix such that there is a smooth transition between the core member and the coil wire helix. A problem with Hawkins is that the flexibility of the core member changes abruptly at the reduced diameter stepped down portion. Another problem with Hawkins is that the radioscopic image has a single radioscopic intensity level within the vascular lumen.

An additional technique involving a coiled wire helix is discussed in U.S. Pat. No. 4,832,047 issued to Sepetka et al. Sepetka attempts to solve the same problem that Hawkins solved. That is, Sepetka suggests a method for providing a smooth transition from the proximal end of the coiled wire helix to the core member. Sepetka does this by providing a guidewire having a distal tapered segment and having a distal end coil carried over a portion of the tapered segment. The strand forming the helical wrappings of the coil is reduced in thickness in the region of proximal attachment to the core member, thus maintaining a relatively constant sum diameter of the core member and the coil. A problem with Sepetka is that the coiled wire helix is difficult to manufacture. Anther problem is that the radioscopic image has a single radioscopic intensity level within the vascular lumen.

Another improvement involving a coiled wire helix is discussed in U.S. Pat. No. 5,174,302 issued to Palmer. Palmer suggests an apparatus wherein the coiled wire helix is banded to define portions that are highly radiopaque and portions that are much less radiopaque to X-radiation. This configuration allows post angioplasty X-ray imaging of the blood vessel without removal of the guidewire. Palmer suggests varying the pitch of stainless steel winding to leave gaps between adjacent coils. Later, highly opaque wire coils are interleaved into these gaps before the spring is mounted into the core member. This is a fairly complex manufacturing process. In addition, the flexibility of the core member is not uniformly increased in the direction of the distal tip.

That is, the Palmer apparatus, like Box above, comprises a plurality of uniform diameter segments coupled together with tapered portions.

A coiled wire helix is discussed in U.S. Pat. No. 5,144,959 issued to Gambale et al. Gambale suggests an apparatus wherein there are two coaxial coiled wire helices wrapped around the core member. The inner helix is wrapped around the extreme distal tip of the core member and extending distally therefrom. The inner helix is formed from a highly radiopaque material. The portion of the core member that is disposed within the outer helix is plated with a radiopaque material. When viewed under fluoroscopy, the highly radiopaque coil defines a dark image whereas the more proximal plated portion of the core member defines a moderately radiopaque image. A problem with Gambale is that two separate coils must be used along with an electroplating process. Also, the flexibility of the core member is not uniformly increased in the direction of the distal tip.

A further approach involving a coiled wire helix is discussed in U.S. Pat. No. 5,228,453 issued to Sepetka. Sepetka suggests a guidewire having a torquable proximal wire section, a more flexible intermediate section with a flexible polymer type covering, and a most flexible distal end section having a coiled wire helix wrapped therearound. A helical ribbon coil is wrapped about the intermediate core segment between the core member and the polymer tube covering to increase radiopacity and improve torque transmission while retaining flexibility. A problem with Sepetka is that two wire helices are required along with a polymer covering. Also, the flexibility of the core member is not uniformly increased in the direction of the distal tip.

SUMMARY OF THE INVENTION

The present invention overcomes the above described problems by providing an improved catheter guidewire including proximal and distal sections, the distal section preferably comprising various segments wherein each segment has a tapered diameter. A helical coil may be used to encase or cover the tip end of the distal section thereby providing column strength while maintaining lateral flexibility. A predetermined number of distal segments of the core member may be flattened to further increase the flexibility of the distal end of the core member.

In one embodiment of the present invention, a core member having a continuously decreasing diameter is employed. The core member may comprise a plurality of segments wherein each segment tapers at a constant rate. The plurality of segments may individually have a different taper rate than adjoining segments. This configuration provides a uniform change in flexibility within a given segment while providing a change in the flexibility rate at the interface between the segments. This configuration combines the advantage of a uniform flexibility change with the ability to alter the flexibility characteristics at predetermined points along the core member to optimize guidewire performance. The preferred mode of the present invention is to have the core member manufactured from a continuous element and not separate elements that are adjoined together.

In another embodiment of the present invention, a distal portion of the core member may be flattened. That is, the decreasing diameter wire may be flattened to provide even greater flexibility at the distal tip of the core member. In addition, the flattened distal tip may provide a base for attaching the distal tip of the core member to a wire coil helix (see below).

A coiled wire helix may be provided at the distal tip of the core member. The proximal end of the wire helix may be attached to the core member at a predetermined distance from the distal end of the core member. The distal end of the wire helix may be attached to the distal end of the core member. The attachment means may include solder, baize, adhesive, or any other attachment means.

A first embodiment of the coiled wire helix of the present invention comprises a stainless steel wire which is close wound at a proximal end and space wound at a distal end. There may be a transition portion between the close wound region and the space wound region. The proximal end, distal end, and transition portion of the wire helix may be attached to a corresponding surface of the core member. The space wound portion of the wire helix may be plated with gold or other radioscopic material to improve the radioscopic image of the apparatus. The wire used to form the helix has an essentially round cross section.

Another embodiment of the present invention is similar to the previous embodiment except that the outer surface of the close wound portion of the wire helix is ground flat. In addition, the wire used to form the helix may be made from gold, platinum, or any other radioscopic material. Both the shape and material used in the wire improves the visibility of the fluoroscopic image of the proximal portion of the wire helix. Since the distally located space wound region of the coil helix may not be ground flat in this embodiment, there may be a transition region positioned between the close wound region and the space wound region. In this transition region the windings of the wire helix may be ground flat to some degree.

Another embodiment of the present invention is similar to the previous embodiment except that the cross section of the wire used to form the wire helix has an essentially rectangular shape. That is, the wire used may be a flat ribbon rather than a round wire for both the close wound region and the space wound region of the wire helix. The flat ribbon yields different flexibility characteristics and also provides a brighter radioscopic image. In the preferred mode, the ribbon wire is made from gold, platinum, or any other radioscopic material. The distal portion of the space wound region of the wire helix may continue to be wound proximally around the original winding back to the transition region. That is, there may be an original space wound winding extending from the transition region to the distal end of the wire helix. There may also be a secondary space winding coaxial with the original space winding extending proximally from the distal end of the wire helix back to the transition region. The secondary winding may extend either internal or externally to the original space winding.

The wire helix embodiment discussed above may be mounted on the continuously decreasing diameter core member. The distal end of the wire helix may be attached to the distal tip of the core member via a solder ball or other attachment means. The proximal end of the wire helix may be attached to a predetermined surface of the continuously decreasing diameter core member located proximally of the distal end of the core member. Finally, the transition region of the wire helix may be attached to a corresponding surface of the core member to strengthen and stiffen the transition region as needed.

BRIEF DESCRIPTION OF THE DRAWINGS

The objects and many of the attendant advantages of the present invention will be readily appreciated as it becomes better understood by reference to the following detailed description when considered in connection with the accompanying drawings, in which like reference numerals designate like parts throughout the figures thereof and wherein:

FIG. 3, comprising

DETAILED DESCRIPTION OF THE PREFERRED EMBODIMENTS

Figure 1:
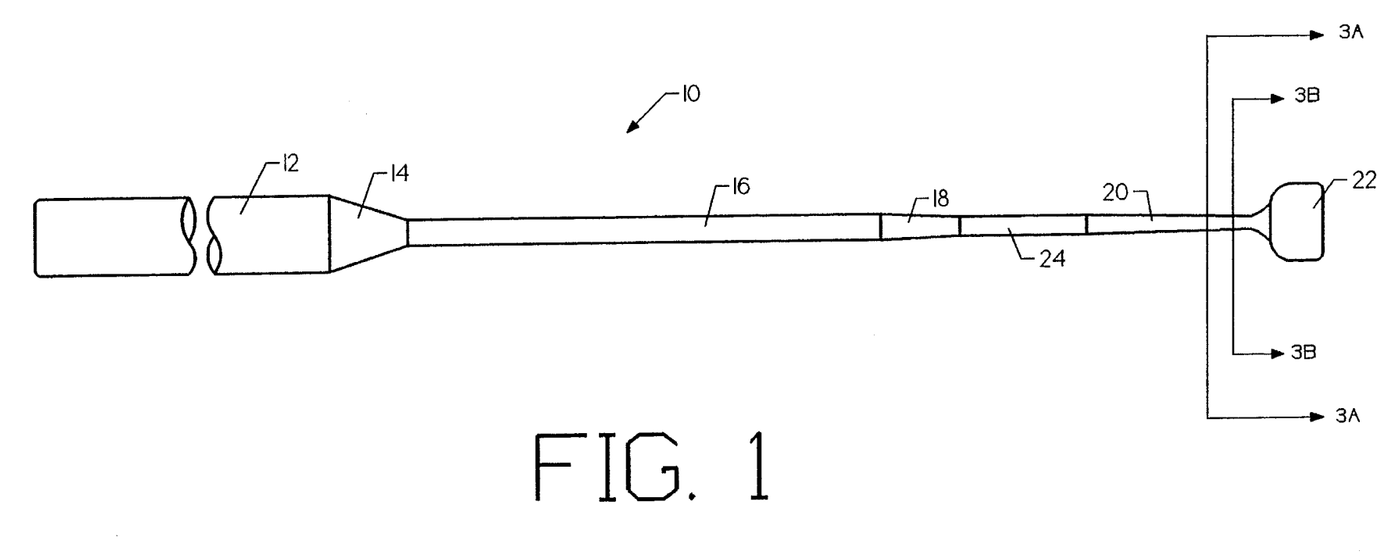
FIG. 1 is a plan view of a first embodiment of the core wire of the present invention.

FIG. 1 is a plan view of a first embodiment of core wire 10, incorporated into the present invention. The preferred embodiments include a core wire, such as core wire 10, with a special helix (described below) attached to the distal end.

Core wire 10 is preferably formed of a length (i.e., about 200 centimeters) of #304 stainless steel. The extended proximal portion 12 is about 150 centimeters of constant diameter of about 0.014 inch or 0.018 inch. It may be completely coated with a lubricous coating to lessen friction within the lumen of a catheter.

Taper 14 and the remaining distal portion of core wire 10 is produced by centerless grinding the length of stainless steel wire. Isodiametric portion 16 has a diameter of about 0.006 inch. A second taper 18 couples to isodiametric portion 24, which is in turn coupled to tapered portion 20 having its distal end formed into a ribbon as described below in greater detail. Distal tip 22 has a diameter of about that of proximal portion 12. It is used for terminating the distal portion of the helix (not shown in this view).

Figure 2:
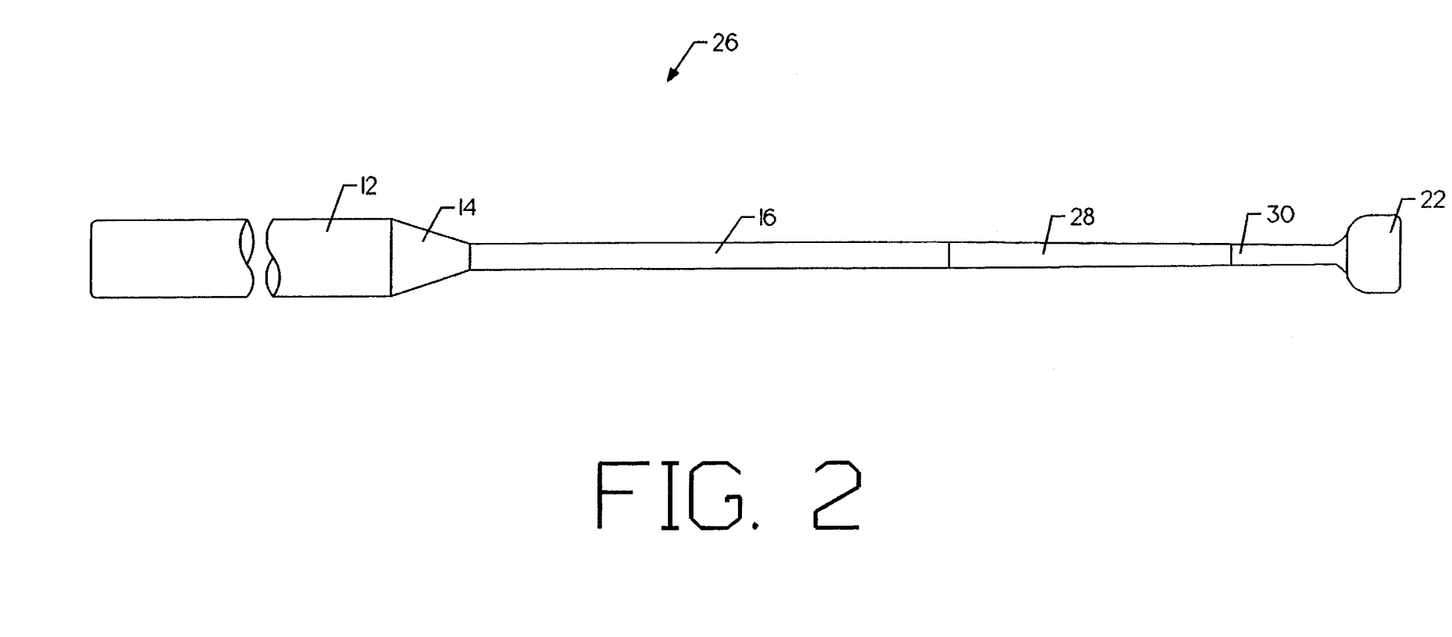
FIG. 2 shows an alternative embodiment of a core wire.

FIG. 2 shows a preferred alternative embodiment of the core wire 26. The proximal portion 12 and distal tip 22 are as previously described. However, the remaining length is tapered and has no other isodiameter portions. It has been found that this may improve the handling characteristics of the completed structure as there are no corresponding abrupt changes in core wire diameter. However, to improve control of the changes in flexibility from proximal to distal ends, there are employed a number of tapers of differing slopes. As shown, tapers 14, 16, and 28 each employ a different slope. Taper 30 is formed into a tapered ribbon as is described in more detail below.

Figure 3A:
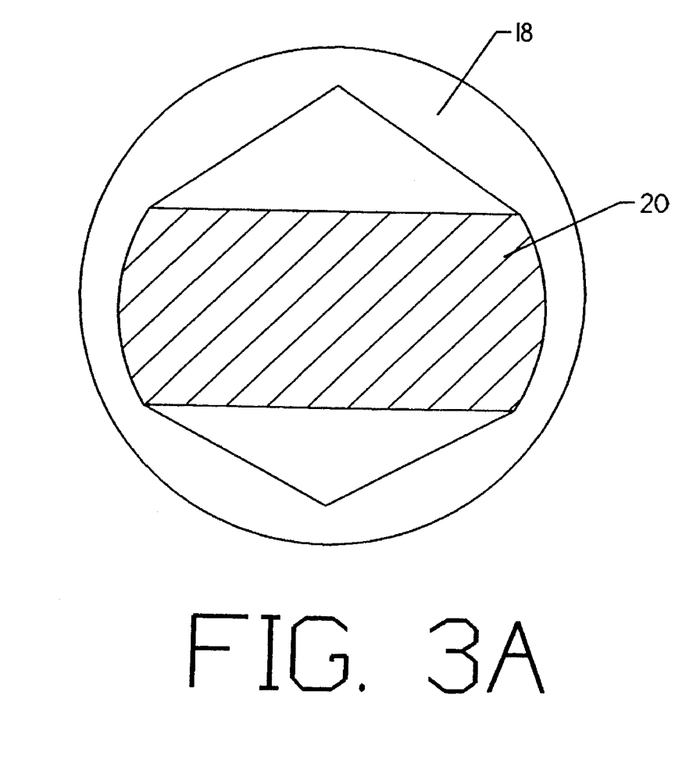
FIG. 3A and FIG. 3B show sections of the tapered distal ribbon of the first embodiment of the core wire.

FIG. 3A is a sectioned view showing tapered ribbon 20 as it proceeds distally toward distal tip 22 (see also FIG. 1).

Figure 3B:
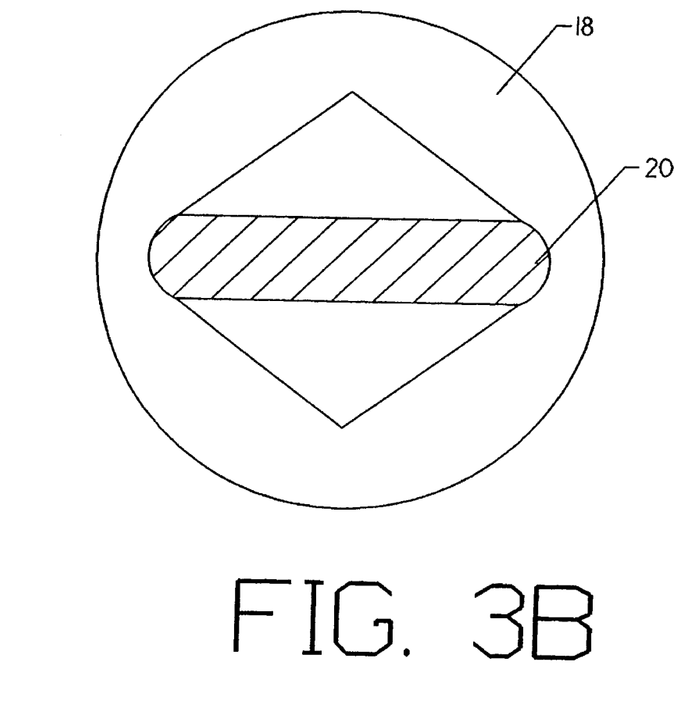

FIG. 3B is a sectioned view taken distally of FIG. 3A. As can be seen, ribbon 20 becomes differentially more flexible in the distal direction as the minor axis is decreased.

Figure 4:
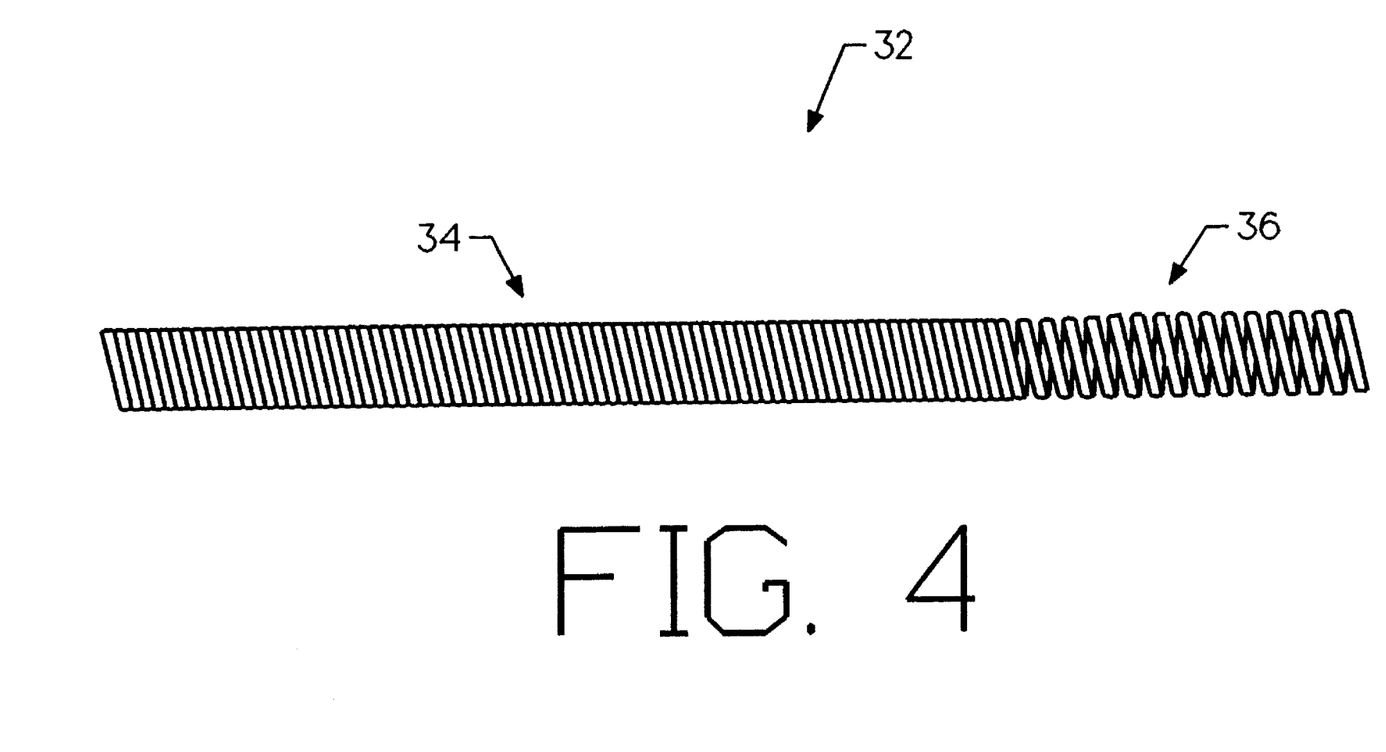
FIG. 4 is a view of a first embodiment of the distal coil of the present invention.

FIG. 4 is a plan view of a first embodiment of distal helix 32 which is attached to one of the core wire embodiments as described in greater detail below. Preferably distal helix 32 is a simple coil of #304 stainless steel wire having a circular cross section. The wire has a diameter of about 0.002 inch and the completed helix has an outside diameter approximately equal to the diameter of proximal portion 12 of the core wire (see also FIGS. 1 and 2).

Proximal length 34 of distal helix 32 is close wound as shown. Distal length 36 is space wound as shown to increase flexibility in the very distal region. Distal length 36 is plated with gold or another heavy metal to improve visibility under radioscopic observation. Proximal length may be similarly plated to a lesser thickness, if desired to provide a smoother transition from light to dark of the radioscopic image.

Figure 5:
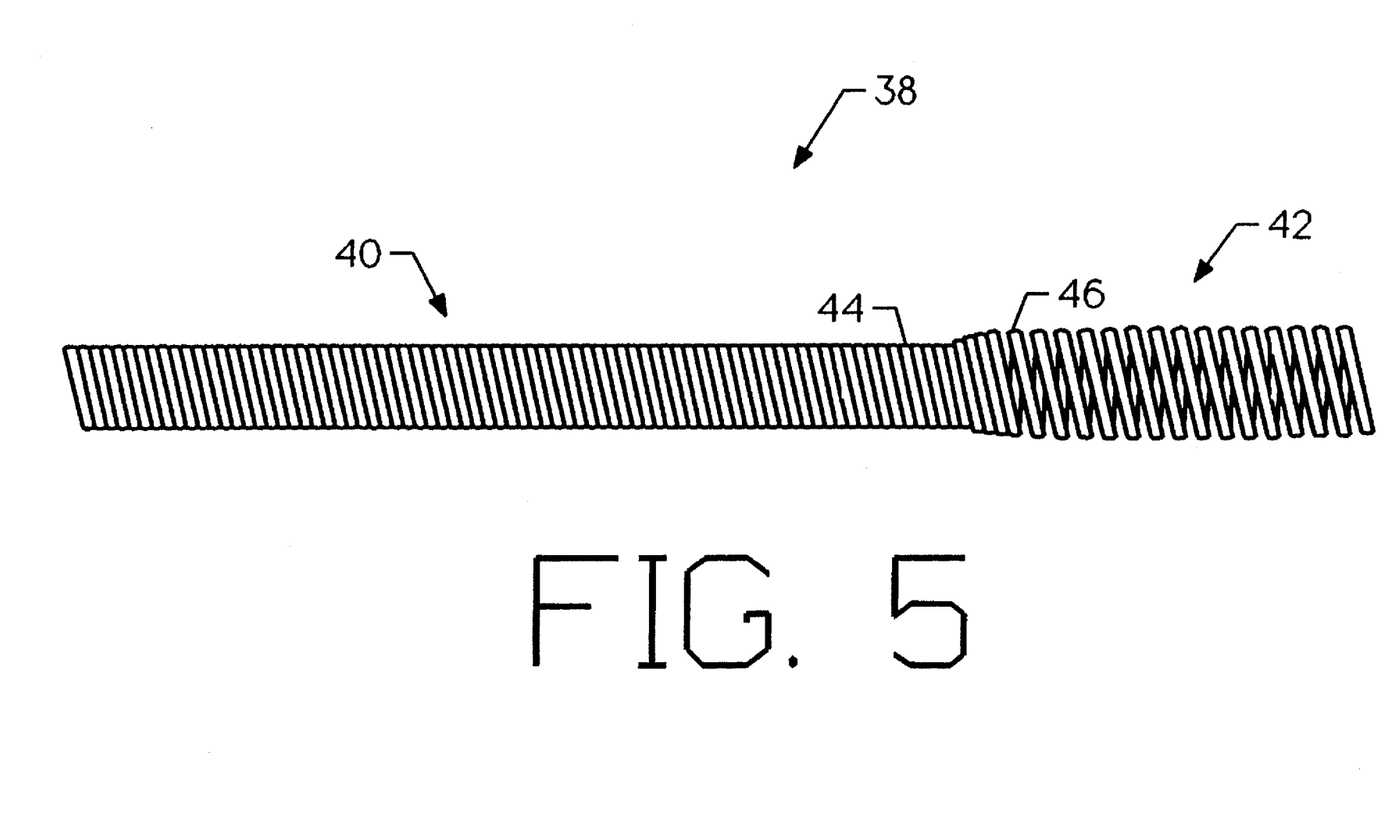
FIG. 5 shows a second embodiment of the distal coil.

FIG. 5 is a alternative embodiment of a distal helix 38. It is preferably made of 14k gold wire of a circular cross section. Other heavy metals having appropriate radioscopic properties would also be suitable. Proximal length 40 is close wound whereas distal length 42 is space wound as in the previously discussed embodiment.

Proximal length 40 is ground flat at its outer periphery as shown. This increases the flexibility and reduces the radioscopic image. Therefore, the resulting structure produces a bright image along distal length 42 and a darker but distinctly visible image along proximal length 40. Transition zone 44 ensures that the grinding process does not produce a sufficiently abrupt change between proximal length 40 and distal length 42 to structurally weaken the transition point.

Figure 6:
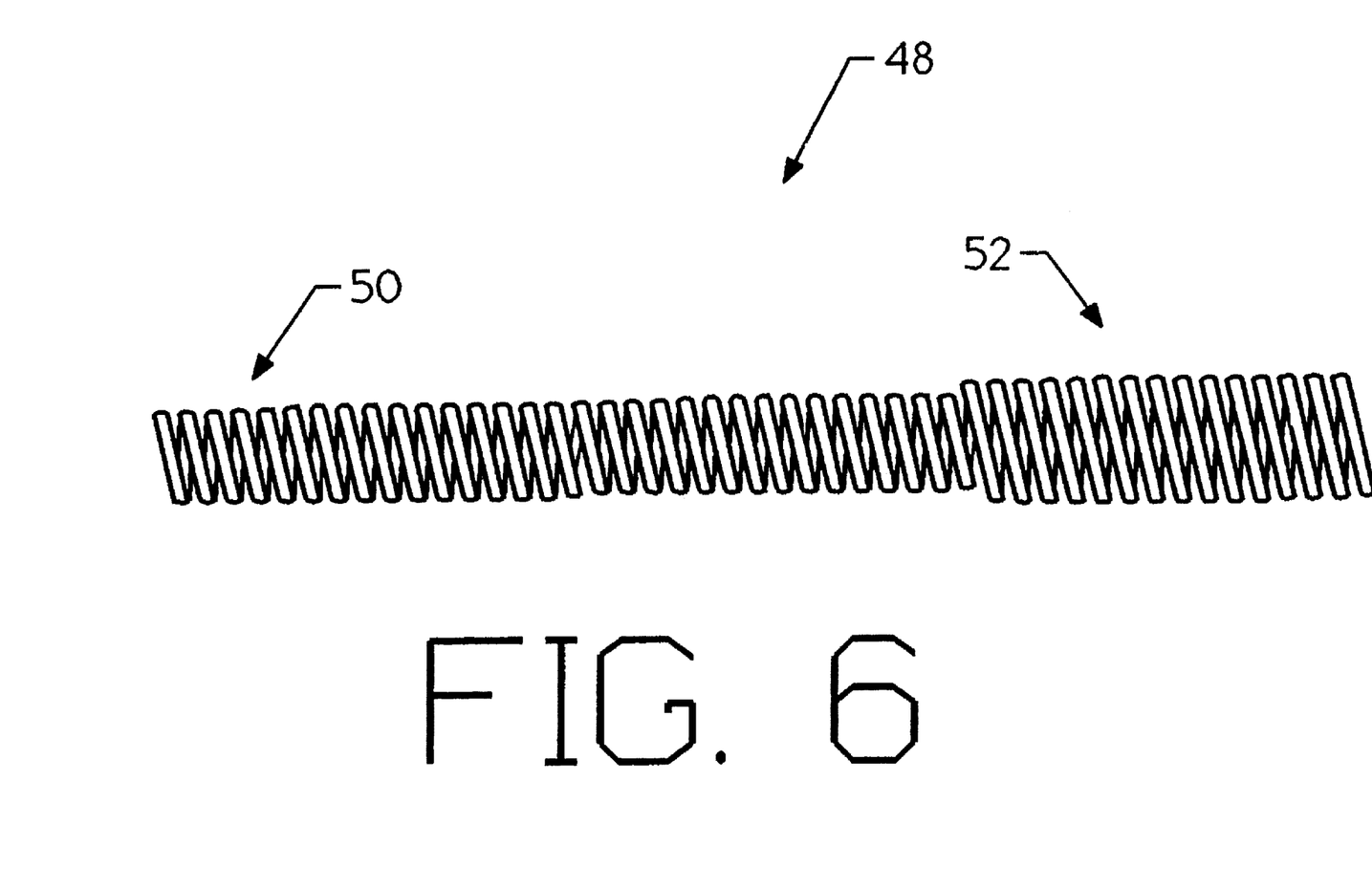
FIG. 6 shows a third embodiment of the distal coil.

FIG. 6 shows a further embodiment of the distal helix. Preferably, distal helix 48 is formed of a flattened platinum ribbon which is space wound about its entire length. Proximal length 50 is space wound to prevent it from appearing too bright under radioscopic observation.

To enhance the brightness of distal length 52, the platinum ribbon is doubled over from the distal end along distal length 52 as shown. In this way, distal length 52 contains a double thickness of the platinum ribbon, to ensure that its radioscopic pattern appears distinctly brighter.

Figure 7:
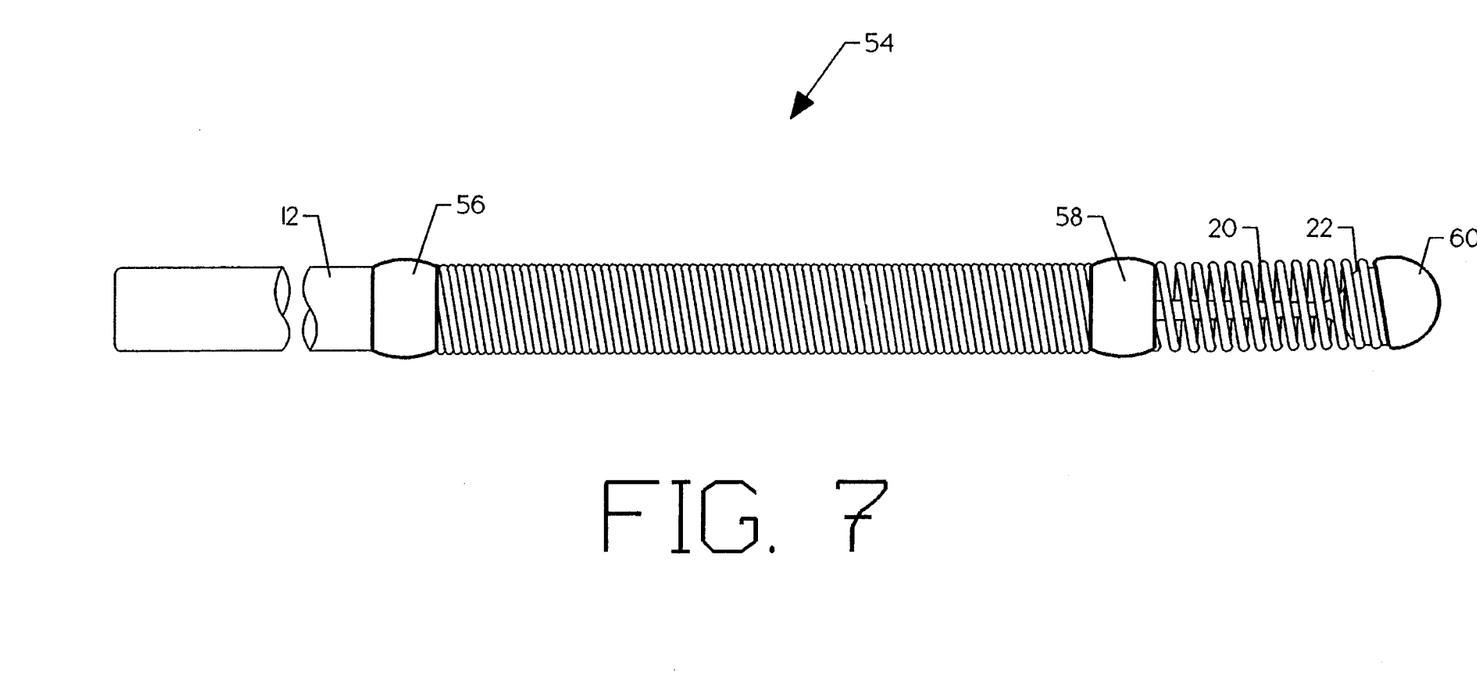
FIG. 7 is a plan view of a guide wire according to the present invention employing the first embodiment of the distal coil.

FIG. 7 shows an assembled guide wire 54 employing core wire 10 (see also FIG. 1) and distal helix 32 (see also FIG. 4). Ball tip 60 is formed by soldering or brazing over distal helix 32 and distal tip 22 of core wire 10, thus permanently joining them. Reenforcing points 56 and 58 are similarly soldered or brazed to complete the attachment of distal helix 32 to core wire 10. Reenforcing point 56 is located at the proximal end of taper 14 (see also FIG. 1) and reenforcing point 58 is located at the intersection of proximal length 34 and distal length 36 (see also FIG. 4).

Figure 8:
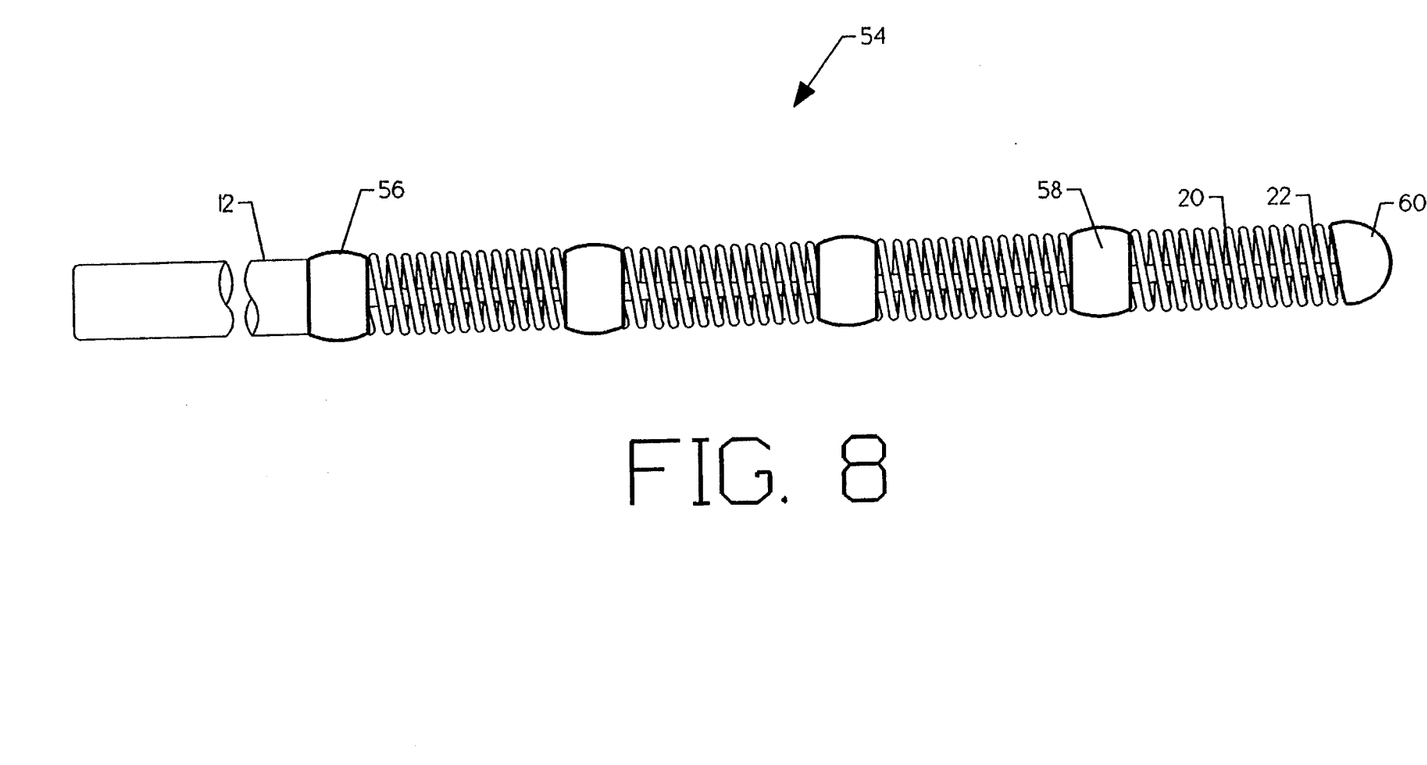
FIG. 8 shows a guide wire employing the third embodiment of the distal coil.

FIG. 8 is a view of guide wire 60 incorporating core wire 26 (see also FIG. 2) and distal helix 48 (see also FIG. 6). Ball tip 70, reenforcing point 68, and reenforcing point 62 are formed as discussed above for the embodiment of FIG. 7. However, because distal helix 48 is space wound over its entire length, additional reenforcing points are required. Therefore, reenforcing points 64 and 66 are established at convenient points along tapers 16 and 28 (see also FIG. 2).

It can be readily seen that other combinations of the two core wire embodiments and three distal helix embodiments can be employed to provide a guide wire having the desired properties.

Having thus described the preferred embodiments of the present invention, those of skill in the art will readily appreciate other useful embodiments within the scope of the attached claims.

I claim:

1. A guide wire for use in medical procedures comprising:
   a. an elongate core wire having a proximal end and a distal end, the core wire including a tapered ribbon portion; and
   b. a distal helix having a proximal end and a distal end wherein said distal end of said distal helix is fixedly attached to said distal end of said core wire and said distal helix includes means for providing a brighter radioscopic image at said distal end of said distal helix than at said proximal end of said distal helix.

2. A guide wire according to claim 1 wherein said core wire further comprises a proximal portion having a constant diameter and a distal portion having a reduced diameter.

3. A guide wire according to claim 2 wherein said distal helix is fixedly attached over said distal portion of said core wire.

4. A guide wire according to claim 3 wherein said distal portion of said core wire has a proximal end and a distal end and wherein said distal portion tapers from proximal end of said distal portion to said distal end of said distal portion.

5. A guide wire according to claim 3 wherein said distal portion of said core wire includes at least one reduced diameter isodiametric portion.

6. A guide wire according to claim 1 wherein said tapered ribbon portion tapers from a proximal direction to a distal direction.

7. A guide wire according to claim 1 wherein said distal helix comprises a length which is close wound, a length which is space wound, and a transition region; the transition region separates the close wound length and the space wound length.

8. A guidewire for use in a medical procedure, comprising:

an elongate core wire having a proximal end and a distal end;

a distal helix having a proximal end and a distal end wherein said distal end of said distal helix is fixably attached to said distal end of said core wire and said distal helix includes means for providing a brighter radioscopic image at said distal end of said distal helix than at said proximal end of said distal helix; and said distal helix being formed from a wire strand that is ribbon shaped, wherein the wire strand is doubled over from the distal end of the distal helix along a portion of the length of the distal helix.

9. A guide wire according to claim 8 wherein the wire strand is made from gold.

10. A guide wire according to claim 8 wherein the wire strand is made from platinum.

11. A guide wire according to claim 8 wherein said distal helix comprises a flattened ribbon which is space wound about its entire length.

* * * * *